United States Patent
Ma et al.

(10) Patent No.: US 9,763,636 B2
(45) Date of Patent: Sep. 19, 2017

(54) METHOD AND SYSTEM FOR SPINE POSITION DETECTION

(71) Applicants: KONINKLIJKE PHILIPS N.V., Eindhoven (NL); SHENYANG NEUSOFT MEDICAL SYSTEMS CO., LTD., Liaoning (CN)

(72) Inventors: Yue Ma, Shenyang (CN); Yanhua Shen, Shenyang (CN); Dan Zhao, Shenyang (CN)

(73) Assignees: KONINKLIJKE PHILIPS N.V., Eindhoven (NL); SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 0 days.

(21) Appl. No.: 14/915,359

(22) PCT Filed: Sep. 17, 2014

(86) PCT No.: PCT/IB2014/064573
§ 371 (c)(1),
(2) Date: Feb. 29, 2016

(87) PCT Pub. No.: WO2015/040547
PCT Pub. Date: Mar. 26, 2015

(65) Prior Publication Data
US 2016/0210740 A1    Jul. 21, 2016

(30) Foreign Application Priority Data

Sep. 17, 2013  (CN) .......................... 2013 1 0425701
Aug. 18, 2014  (WO) ................ PCT/CN2014/084633

(51) Int. Cl.
*G06K 9/00*  (2006.01)
*A61B 6/00*  (2006.01)
(Continued)

(52) U.S. Cl.
CPC .............. *A61B 6/505* (2013.01); *A61B 6/032* (2013.01); *A61B 6/5211* (2013.01); *G06T 7/10* (2017.01);
(Continued)

(58) Field of Classification Search
CPC ..................................................... A61B 6/505
See application file for complete search history.

(56) References Cited

U.S. PATENT DOCUMENTS 5,577,089 A    11/1996  Mazess
7,491,180 B2    2/2009  Pacheco
(Continued)

FOREIGN PATENT DOCUMENTS

WO    2008/030247    3/2008
WO    2011/021181    2/2011

OTHER PUBLICATIONS

Dong, et al., "Automated Vertebra Identification from X-Ray Images", ICIAR 2010, Part II, LNCS 6112.
(Continued)

*Primary Examiner* — Oneal R Mistry (57) ABSTRACT

The present invention provides a method for spine position detection, comprising: obtaining 2D geometrical configuration of a current vertebra body selected from a plurality of vertebra bodies visible in an image on a sagittal plane defined by a horizontal component of an initial point, a geometrical template being applied to the current vertebra body and the 2D geometrical configuration of the current vertebra body being adjusted by a predetermined correlation evaluation; searching adjacent edge points of next vertebra body corresponding to a number of edge points of the current vertebra body by identifying the gradient values along the direction substantially perpendicular to the edge of the current vertebra body based on the adjusted 2D geo- (Continued)

metrical configuration of the current vertebra body; calculating height of an intervertebral disc located between the current vertebra body and the next vertebra body based on an average of the distances between the edge points of the current vertebra body and the corresponding adjacent edge points of the next vertebra body; determining 2D geometrical configuration of the next vertebra body based on the height of the intervertebral disc and the adjusted 2D geometrical configuration of the current vertebra body. Then the transverse images of the intervertebral discs can be formed to serve for diagnosis.

16 Claims, 10 Drawing Sheets (51) Int. Cl.
- *A61B 6/03* (2006.01)
- *G06T 7/70* (2017.01)
- *G06T 7/10* (2017.01)
- *G06T 7/12* (2017.01)
- *G06T 7/149* (2017.01)

(52) U.S. Cl.
CPC ............... *G06T 7/12* (2017.01); *G06T 7/149* (2017.01); *G06T 7/70* (2017.01); *A61B 6/5217* (2013.01); *G06T 2207/10081* (2013.01); *G06T 2207/30012* (2013.01)

(56) References Cited

U.S. PATENT DOCUMENTS

| | | |
|---|---|---|
| 7,561,728 B2 | 7/2009 | Abufadel |
| 8,676,298 B2 | 3/2014 | Wang |
| 2002/0136437 A1* | 9/2002 | Gerard ............... G06T 7/60 382/128 |
| 2003/0086596 A1 | 5/2003 | Hipp |
| 2006/0120583 A1* | 6/2006 | Dewaele ............ G06T 3/0068 382/128 |
| 2007/0121778 A1 | 5/2007 | Shen |
| 2009/0202122 A1 | 8/2009 | Wang |
| 2009/0297012 A1 | 12/2009 | Brett |
| 2011/0064291 A1 | 3/2011 | Kelm |
| 2012/0143090 A1* | 6/2012 | Hay ................ A61B 6/505 600/587 |
| 2013/0108134 A1 | 5/2013 | Luo |
| 2013/0131486 A1* | 5/2013 | Copf ............... A61B 5/1079 600/407 |
| 2013/0202179 A1 | 8/2013 | Illes |
| 2013/0230224 A1 | 9/2013 | Claude |
| 2014/0046169 A1 | 2/2014 | Liu |

OTHER PUBLICATIONS

Dong, et al., "Automated Intervertebral Disc Detection from Low Resolution, Sparse MRI Images for the Planning of Scan Geometries", MLMI 2010, LNCS 6357.

* cited by examiner

METHOD AND SYSTEM FOR SPINE POSITION DETECTION

CROSS REFERENCE TO RELATED APPLICATIONS

This application is the U.S. National Phase application under 35 U.S.C. §371 of International Application No. PCT/IB2014/064573 filed Sep. 17, 2014, published as WO 2015/040547 on Mar. 26, 2015, which claims the benefit of Chinese Patent Application Number 201310425701.5 filed Sep. 17, 2013 and Chinese Patent Application Number PCT/CN2014/084633 filed Aug. 17, 2014. These applications are hereby incorporated by reference herein.

FIELD OF THE INVENTION

The present disclosure relates to digital image processing, and more particularly to a system and method for spine position detection.

BACKGROUND OF THE INVENTION

The digital imaging technology has experienced significant growth in recent years. Examples of such growth include the development of using computers for assisting analysis of spines in radiography. In a clinical examination, transverse image is usually used for detecting an abnormality of an inter-vertebral disk. Position and orientation of intervertebral disc are important anatomies for the diagnosis.

Currently, measurements in the clinical examination need human interaction, one example as a CT scanner with a gantry which cannot be rotatable. Usually, positions and orientations of intervertebral discs are placed manually on the spine for such CT scanner. Manual measurement is not only time-consuming, but also subject to errors depending on the person's skill, experience and other human factors.

SUMMARY OF THE INVENTION

Therefore, a need exists for a method and system for spine position detection that require less human interaction.

According to an embodiment of the present disclosure, a method for spine position detection, comprising: obtaining 2D geometrical configuration of a current vertebra body selected from a plurality of vertebra bodies visible in an image on a sagittal plane defined by a horizontal component of an initial point, a geometrical template being applied to the current vertebra body and the 2D geometrical configuration of the current vertebra body being adjusted by a predetermined correlation evaluation; searching adjacent edge points of next vertebra body corresponding to a number of edge points of the current vertebra body by identifying the gradient values along the direction substantially perpendicular to the edge of the current vertebra body based on the adjusted 2D geometrical configuration of the current vertebra body; calculating height of an intervertebral disc located between the current vertebra body and the next vertebra body based on an average of the distances between the edge points of the current vertebra body and the corresponding adjacent edge points of the next vertebra body; determining 2D geometrical configuration of the next vertebra body based on the height of the intervertebral disc and the adjusted 2D geometrical configuration of the current vertebra body.

In one aspect, the geometrical template is a rectangular template with 2D parameter values on the sagittal plane.

In another aspect, the predetermined correlation evaluation comprises a particle filtering.

According to another embodiment of the present disclosure, a system for spine position detection, comprising: a program storage device readable by machine, tangibly embodying a program of instructions executable by the machine to perform above methods.

The results of experiments show that, according to techniques described herein, accuracy and speed of the measurement are improved since human interaction during the spine position detection is much reduced.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present disclosure will be described and explained hereinafter in more detail in combination with solutions and with reference to the drawings, wherein.

The same reference signs in the figures indicate similar or corresponding feature and/or functionality.

DETAILED DESCRIPTION

The present invention will be described with respect to particular solutions and with reference to certain drawings but the invention is not limited thereto but only by the claims. The drawings described are only schematic and are non-limiting. In the drawings, the size of some of the elements may be exaggerated and not drawn on scale for illustrative purposes.

Figure 1:
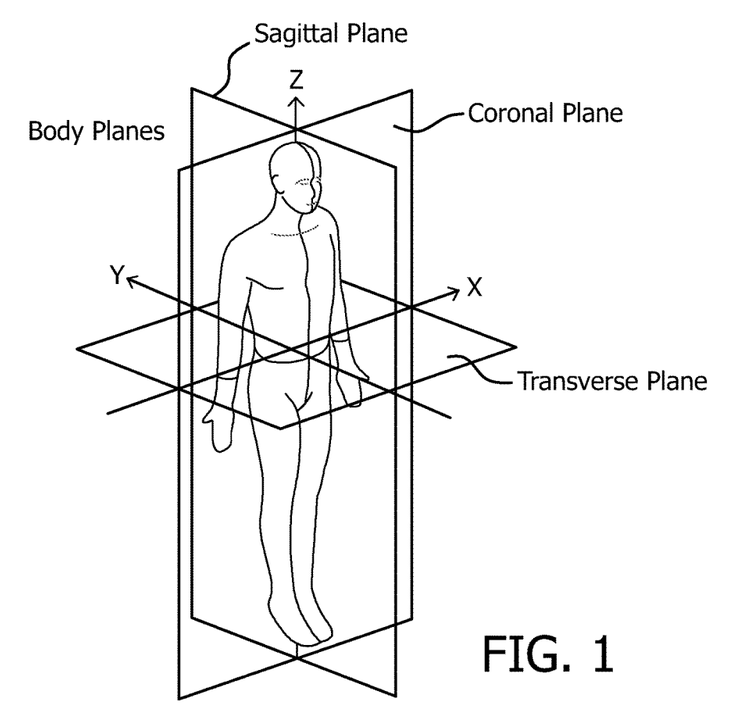
FIG. 1 is a diagram of standard anatomical position defined for human anatomy.
Figure 2:
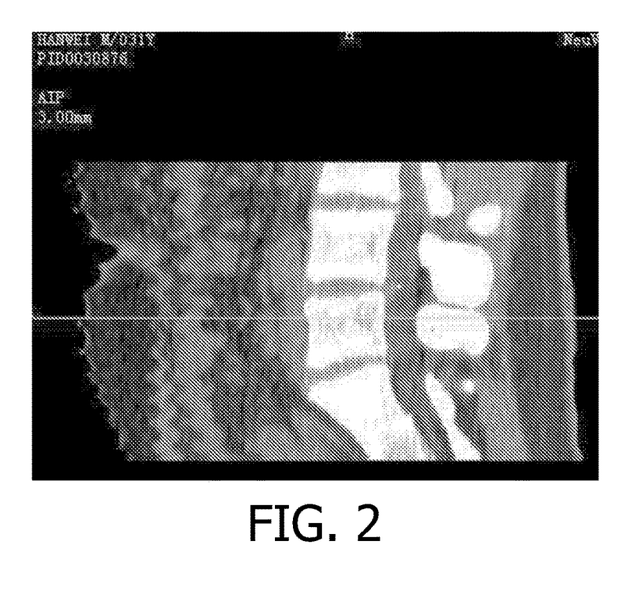
FIG. 2 is a sagittal view of visible vertebra bodies according to one embodiment of the present disclosure.

FIG. 1 shows standard anatomical position defined for human anatomy. In a measurement, among a number of visible vertebral bodies of a spine (also called as vertebral column) as shown in FIG. 2, the last vertebral body is selected by a user (e.g. a physical clinician) as the initial vertebra body. Further, a point P indicated on center of the last vertebral body is selected as the initial point with three coordinate components (horizontal component $P_x$, vertical component $P_y$, axial component $P_z$) in the three-dimensional (3D) Cartesian coordinate system.

Figure 3A:
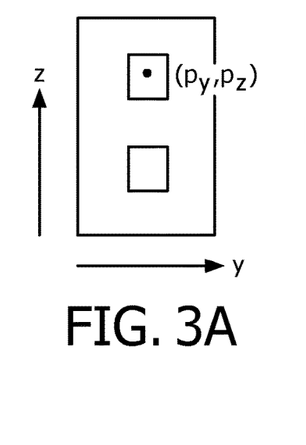
FIG. 3A is an illustration of vertebra bodies on a sagittal plane.
Figure 3B:
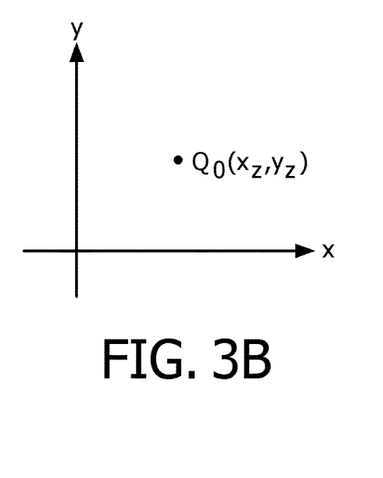
FIG. 3B is an illustration of the center of last vertebra body in a Cartesian coordinate system.

In one embodiment, the coordinate value of the midpoint placed on a line along horizontal direction in an image on a transverse plane is specified as the horizontal component $P_x$. In an image on a sagittal plane defined by $P_x$ (as shown in FIG. 2), the coordinate values of the center of the last vertebral body are specified as vertical component $P_y$ and axial component $P_z$, as shown in FIG. 3A. In medical application, the sagittal plane is used commonly. Therefore, the vertical component $P_y$ and the axial component $P_z$ can be converted to $x_z$ and $y_z$ respectively to define a point $Q_0$ $(x_z, y_z)$ in a two dimensional (2D) coordinate system such as a Cartesian coordinate system as shown in FIG. 3B. Herein the horizontal direction and the vertical direction on the sagittal plane can be referred as the converted horizontal direction and the converted vertical direction.

Figure 4:
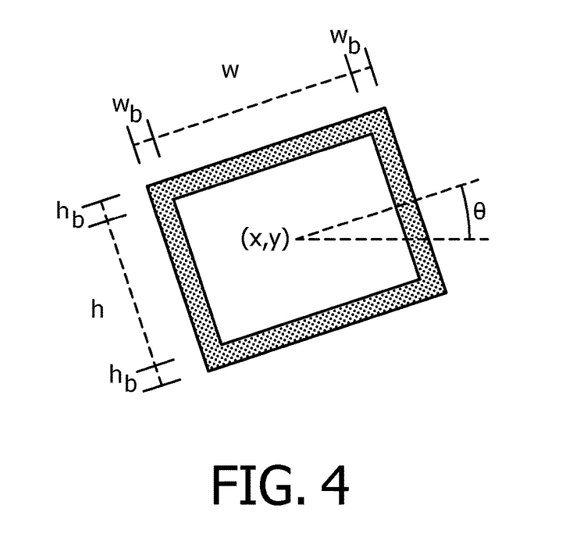
FIG. 4 is a sagittal view of the last vertebral body which is approximated by a rectangle template.

In the present disclosure, a geometrical template is applied to the spine. Since the shape of the vertebral body or the intervertebral disc is similar to a rectangular band, in one embodiment, a rectangular template with 2D parameter values is provided as one example of the geometrical template. Referring to FIG. 4, the 2D geometrical configuration of a vertebra body (i.e. 2D geometrical parameters of the rectangular template) comprises: center (x, y), width w, height h and orientation θ of the rectangular template wherein θ is the angle between the upper edge or lower edge of the rectangular template and the horizontal direction. $Q_0$ $(x_z, y_z)$ is specified as the center (x, y). The width w and the height h are specified as predetermined values $w_z$ and $h_z$ of normal human. The orientation θ is specified as $θ_z$. Since the last vertebral body is initialized as the current vertebral body, the orientation $θ_z$ is set as zero. As shown in FIG. 4, the 2D geometrical configuration of the vertebra body may further comprise interior width $w_b$ and interior height $h_b$. Normally, $w_b$ and $h_b$ are constant values for a person. While for an intervertebral disc, the 2D geometrical information (i.e. the 2D geometrical parameters of the rectangular template) mainly comprises center, height and orientation of the rectangular template. The 2D geometrical information of the intervertebral disc can be derived from the 2D geometrical configuration of the current vertebral body and the 2D geometrical configuration of the next adjacent vertebral body. The derivation will be described in details later.

After obtaining the 2D geometrical configuration ($Q_0$ $(x_z, y_z)$, $w_z$, $h_z$, $θ_z$) of the current vertebral body. The 2D geometrical configuration is further optimized through a predetermined correlation evaluation. In accordance with the correlation evaluation, the 2D geometrical configuration shall be adjusted so that the rectangular template with the adjusted 2D geometrical parameters would be well matched with the image of the current vertebral body.

As shown in FIG. 4, it appears that the interior area of the vertebra body has a homogeneous intensity distribution; while the intensity distribution of the border region defined by $w_b$ and $h_b$ is clearly demarcated; and the strong gradient values only appear on the border of the rectangular template for the vertebra body. The correlation between the rectangular template and the image of the current vertebral body can be evaluated by the intensity correlation and/or the gradient correlation.

Where the interior region of the rectangular template obeys the Gaussian distribution (i.e. a Gaussian model $N(\mu_i, \sigma_i)$, $\mu_i$ is mean value and $\sigma_i$ is standard deviation), for each pixel s that falls in the interior and border region of the rectangular template, the image appearance value of s is defined as $$p(s|X_i) = e^{-\frac{(I(s)-\mu_i)^2}{2\sigma_i^2}}$$

Wherein I(s) is each pixel's intensity value. The intensity correlation $p_I(I|X_i)$ is defined as $$p_I(I|X_i) = e^{\omega_I c_I^i}$$

Where $c_I^i$ is the cross-correlation between the image appearance values $p(s|X_i)$ and a negative template wherein the interior area of the template is set value 1 and the border region is set value 0; and $\omega_I$ is a weighting factor.

Similar to $p_I(I|X_i)$, the gradient correlation $p_G(I|X_i)$ can be defined as $$p_G(I|X_i) = e^{\omega_G c_G^i}$$

where $c_G^i$ is the cross-correlation between the gradient image values of the observed image in the rectangular template area and a positive template wherein the interior area of the template is set value 0 and the border region is set value 1.

It is preferable to select a rectangular template with the most intensity correlation and/or most gradient correlation as the optimized rectangular template. The 2D geometrical configuration obtained in the initialization can be adjusted or updated by the 2D geometrical parameters of the optimized rectangular template so that the rectangular template for the current vertebral body can match the image of the current vertebral body as closely as possible.

To obtain the optimized rectangular template, in one embodiment, a particle filtering algorithm is used as one example of the predetermined correlation evaluation. The number of the particles is not more than 100 and the range of 2D parameter values for a rectangular template is defined as follows by considering the time consuming during the operation of the particle filtering algorithm:

$$x \in (Q_0 \cdot x - 10 \text{ mm}, Q_0 \cdot x + 10 \text{ mm})$$

$$y \in (Q_0 \cdot y - 5 \text{ mm}, Q_0 \cdot y + 5 \text{ mm})$$

$$w/h \in (1, 1.5)$$

wherein x is the parameter value along the converted horizontal direction on the sagittal plane, $Q_0 \cdot x$ (i.e. $x_z$ in FIG. 3B) is the converted horizontal component of the initial point, y is the parameter values along the converted vertical direction on the sagittal plane, $Q_0 \cdot y$ (i.e. $y_z$ in FIG. 3B) is the converted vertical component of the initial point, w/h, i.e. $w_z/h_z$ in FIG. 4, is width-height ratio of the rectangular template.

The particle which is the most correlated to the image of the current vertebra body is selected as the 2D geometrical parameters of the rectangular template. Based on the rectangular template updated with the selected particle, the 2D geometrical configuration of the next vertebra body can be determined.

Figure 5A:
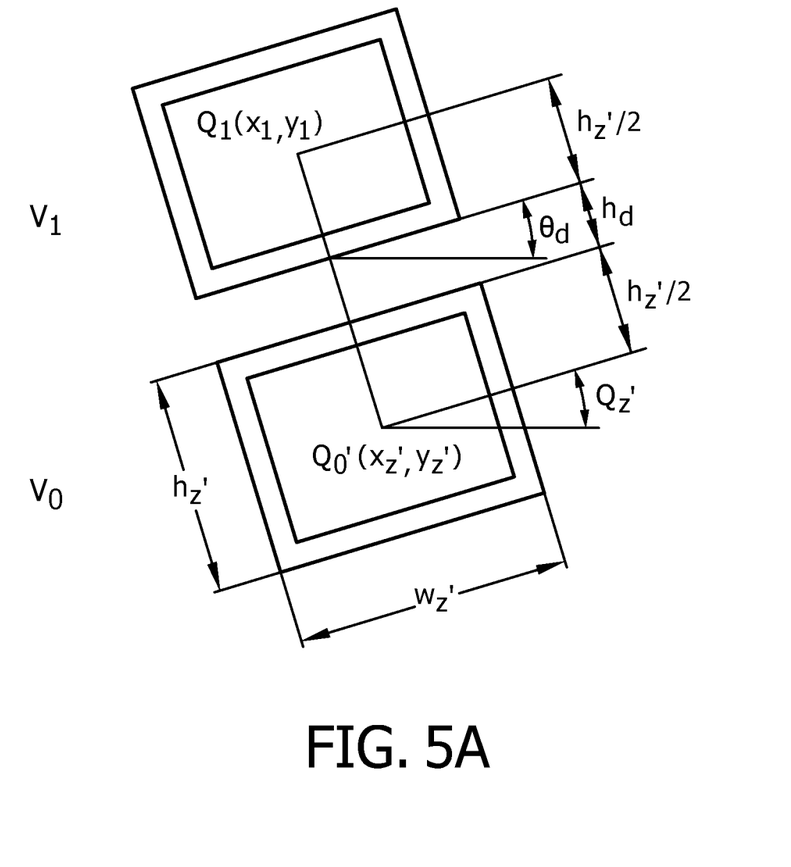
FIG. 5A is an illustration of geometrical parameters of the visible vertebra bodies.

Referring to FIG. 5A, the 2D geometrical configuration $(Q_0 (x_z, y_z), w_z, h_z, \theta_z)$ of the rectangular template of the last vertebra body (called as initial vertebra body $V_0$ herein) is adjusted to $(Q_0' (x_z', y_z'), w_z', h_z', \theta_z')$ with the selected particle. The rectangular template with the adjusted 2D geometrical parameters is also applied to the next vertebra body $V_1$. The next vertebra body $V_1$ is positioned along upward direction and adjacent to the last vertebra body $V_0$.

Figure 5B:
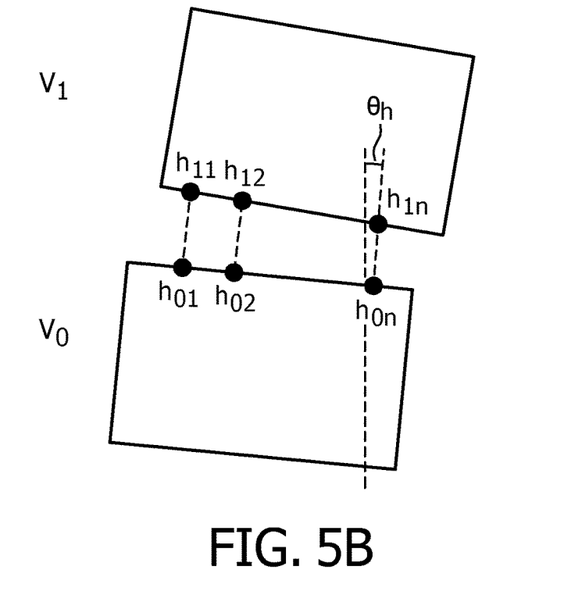
FIG. 5B is an illustration of the height of the intervertebral disc located between the last vertebra body $V_0$ and the next vertebra body $V_1$.

The center $Q_1(x_1, y_1)$ of the rectangular template of the next vertebra body $V_1$ can be calculated as $$x_1 = x_z' + (h_z' + h_d) * \sin \theta_z'$$

$$y_1 = y_z' + (h_z' + h_d) * \cos \theta_z'$$

Wherein $h_d$ is the height of the intervertebral disc located between the last vertebra body $V_0$ and the next vertebra body $V_1$. In one embodiment, $h_d$ can be calculated as the average distance between the upper edge points of the last vertebra body $V_0$ and the corresponding bottom edge points of the next vertebra body $V_1$. As shown in FIG. 5B, based on the adjusted 2D geometrical configuration of the last vertebra body $V_0$, e.g. selecting a plurality of points $h_{01}, h_{02} \ldots h_{0n}$ positioned on the upper edge $w_z'$ of the last vertebra body $V_0$, from these upper edge points $h_{01}, h_{02} \ldots h_{0n}$ of the last vertebra body $V_0$, the corresponding bottom edge points $h_{11}, h_{12} \ldots h_{1n}$ of the next vertebra body $V_1$ can be searched by identifying the gradient values along the direction substantially perpendicular to the upper edge of the last vertebra body $V_0$. Usually, the gradient value of the vertebra body, especially the border of the vertebra body, is quite different from the gradient value of the intervertebral disc. The average distance $h_d$ is obtained as the average of the distance between $h_{01}$ and $h_{11}$, the distance between $h_{02}$ and $h_{12}$ ... and the distance between $h_{0n}$ and $h_{1n}$. The line between upper edge point (e.g. $h_{01}$) of the last vertebra body $V_0$ and the corresponding bottom edge point ($h_{11}$) of next vertebra body $V_1$ has an angle $\theta_h$ with respect to the converted vertical direction. The angle $\theta_h$ equals to the adjusted orientation $\theta_z'$ of the last vertebra body $V_0$.

Then, the next vertebra body $V_1$ can be considered as the current vertebra body. Regarding the 2D geometrical configuration of the current vertebra body (i.e. the next vertebra body $V_1$), the width $w_1$, the height $h_1$ and the orientation $\theta_1$ of the rectangular template for the current vertebra body $V_1$ can be set with the updated 2D geometrical configuration of the last vertebra body $V_0$, i.e. $w_z', h_z', \theta_z'$.

Once obtaining the 2D geometrical configuration $(Q_1 (x_1, y_1), w_1, h_1, \theta_1)$ of the current vertebral body $V_1$, the 2D geometrical configuration is optimized through the predetermined correlation evaluation as well. In one embodiment, by the particle filtering as mentioned above, the 2D geometrical parameters of the rectangular template is adjusted to cause the adjusted 2D geometrical configuration is most matchable with the image of the current vertebral body $V_1$. Based on updated 2D geometrical parameters of the rectangular template, the 2D geometrical configuration of the next current vertebra $V_2$ can be determined in a similar way as mentioned above.

Figure 6:
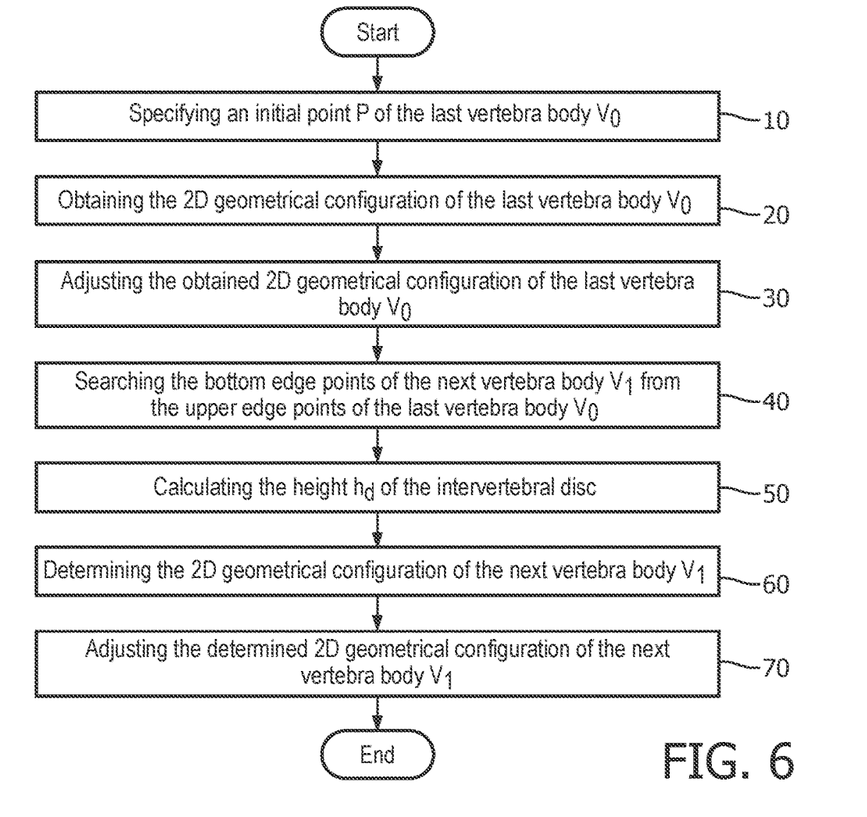
FIG. 6 is a block/flow diagram showing a detection method according to one embodiment of the present disclosure.

FIG. 6 illustrates a block/flow diagram for a detection method mentioned above in accordance with one embodiment of the present disclosure.

In block 10, an image of a part of the spine is specified on the sagittal plane which is defined by the horizontal component $P_x$ of the initial point P ($P_x, P_y, P_z$). The last vertebra body $V_0$ of the spine, as the current vertebra body, is selected by the user as the initial vertebra body (as shown in FIG. 2). The initial point P is specified as the center of the initial vertebra body. A rectangular template as a geometrical template is applied to the image of each of the vertebra bodies which are specified on the sagittal plane.

In block 20, as the current vertebra body, the 2D geometrical configuration $(Q_0 (x_z, y_z), w_z, h_z, \theta_z)$ of the last vertebra body $V_0$ is obtained by identifying the geometrical parameters of the rectangular template. As described in one embodiment shown in FIG. 4, the coordinate values of the center $Q_0 (x_z, y_z)$ can be specified on the sagittal plane; width $w_z$, height $h_z$, and orientation $\theta_z$ are provided with the predetermined values.

In block 30, the obtained 2D geometrical configuration of the last vertebra body $V_0$ is adjusted to $(Q_0' (x_z', y_z'), w_z', h_z', \theta_z')$ by a predetermined correlation evaluation. One embodiment of the predetermined correlation evaluation is the particle filtering algorithm.

In block 40, since the rectangular template with the adjusted 2D geometrical parameters is applied to the next vertebra body $V_1$, based on the adjusted 2D geometrical configuration of the current vertebra body, the adjacent edge points (i.e. the bottom edge points) of the next vertebra body $V_1$ can be searched from the corresponding points (i.e. upper edge points) of the last vertebra body $V_0$, as described in one embodiment shown in FIG. 5B.

In block 50, the height $h_d$ of the intervertebral disc located between the last vertebra body $V_0$ and the next vertebra body $V_1$ can be calculated based on an average of the distances between the searched adjacent edge points of the next vertebra body $V_1$ and the corresponding edge points of the last vertebra body $V_0$.

In block 60, 2D geometrical configuration of the next vertebra body $V_1$ can be determined based on the height $h_d$ of the intervertebral disc and the adjusted 2D geometrical configuration $(Q_0' (x_z', y_z'), w_z', h_z', \theta_z')$ of the last vertebra body $V_0$ as shown in FIG. 5A.

In block 70, once obtaining the 2D geometrical configuration $(Q_1 (x_1, y_1), w_1, h_1, \theta_1)$ of the next vertebra body $V_1$ (considered as the current vertebra body herein), the obtained 2D geometrical configuration is adjusted to $(Q_1' (x_1', y_1'), w_1', h_1', \theta_1')$ by a predetermined correlation evaluation such as particle filtering algorithm.

The adjusted 2D geometrical configuration of the next vertebra body $V_1$, as the current vertebra body, can be served to determine the 2D geometrical configuration of the subsequent vertebra body $V_2$ positioned along the upward direction. The steps in blocks 40-70 are repeated. The 2D geometrical configuration of each vertebra body can be detected in sequence by this way.

Figure 7:
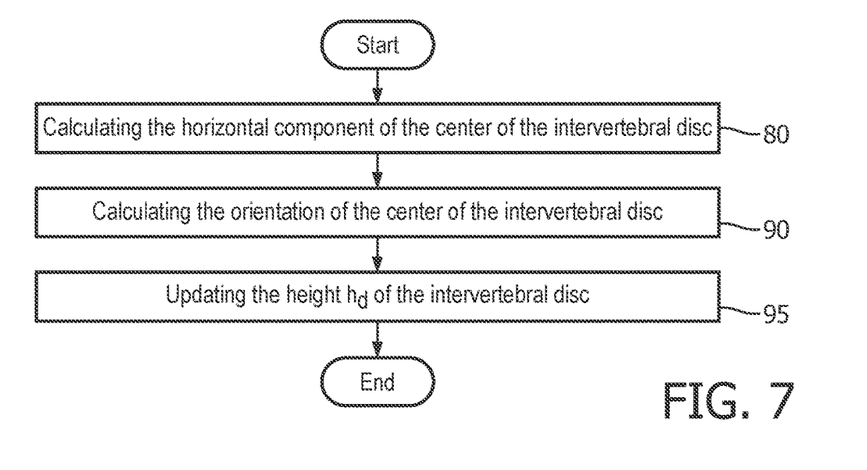
FIG. 7 is a block/flow diagram showing a method for detecting the intervertebral discs according to one embodiment of the present disclosure.

Referring to FIG. 7, a method according to an embodiment of the present disclosure performs a detection of 2D geometrical information of the intervertebral disc.

Figure 5C:
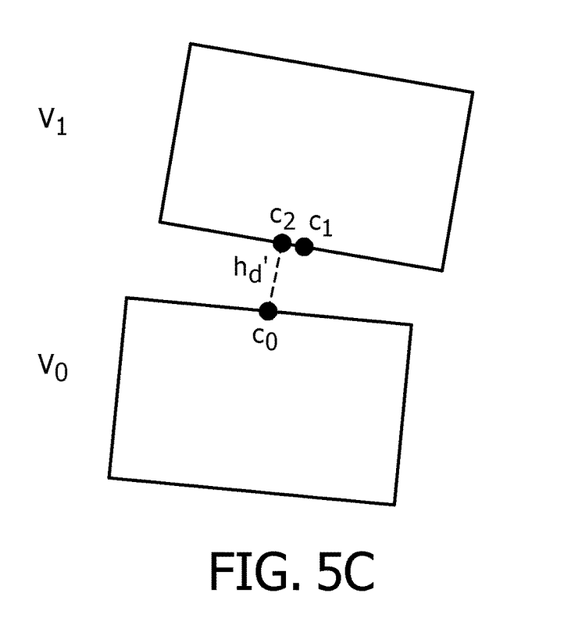
FIG. 5C is an illustration of the average height of the intervertebral disc.

In block 80, since the rectangular template is also applied to the intervertebral disc, the horizontal component $x_d$ of the center of the intervertebral disc $Disk_1$ located between the last vertebra body $V_0$ and the next vertebra body $V_1$ can be calculated as an average of $x_z'$ and $x_1'$, the vertical component $y_d$ of the center of the intervertebral disc $Disk_1$ can be calculated as an average of $y_z'$ and $y_1'$ (as shown in FIG. 5A). In another embodiment as shown in FIG. 5C, the horizontal component $x_d$ of the center of the intervertebral disc $Disk_1$ can be calculated as an average of $c_0$ and $c_1$ wherein $c_0$ is the midpoint of the upper edge of the last vertebra body $V_0$ with the adjusted 2D geometrical configuration and $c_1$ is the midpoint of the bottom edge of the next vertebra body $V_1$ with the adjusted 2D geometrical configuration.

In block 90, the orientation $\theta_d$ of the intervertebral disc $Disk_1$ can be calculated as an average of $\theta_z'$ and $\theta_1'$. Thus, the center $(x_d, y_d)$ and the orientation $\theta_d$ of the intervertebral disc $Disk_1$ can be derived from the adjusted 2D geometrical configuration of the current vertebra body $V_0$ and the adjusted 2D geometrical configuration of the next vertebra body $V_1$.

In block 95, the height $h_d$ of the intervertebral disc located between the last vertebra body $V_0$ and the next vertebra body $V_1$ can be updated based on the adjusted 2D geometrical configuration $(Q_0'$ $(x_z', y_z'), w_z', h_z', \theta_z')$ of the last vertebra body $V_0$ and adjusted 2D geometrical configuration $(Q_1'$ $(x_1', y_1'), w_1', h_1', \theta_1')$ of the next vertebra body $V_1$. In one embodiment, the average distance $h_d$ is updated with the distance $h_d'$ between $c_0$ and $c_2$. Point $c_2$ is one of the bottom edge points of the next vertebra body $V_1$ with the adjusted 2D geometrical configuration. The line between $c_0$ and $c_2$ is substantially perpendicular to the bottom edge of the next vertebra body $V_1$.

Figure 8:
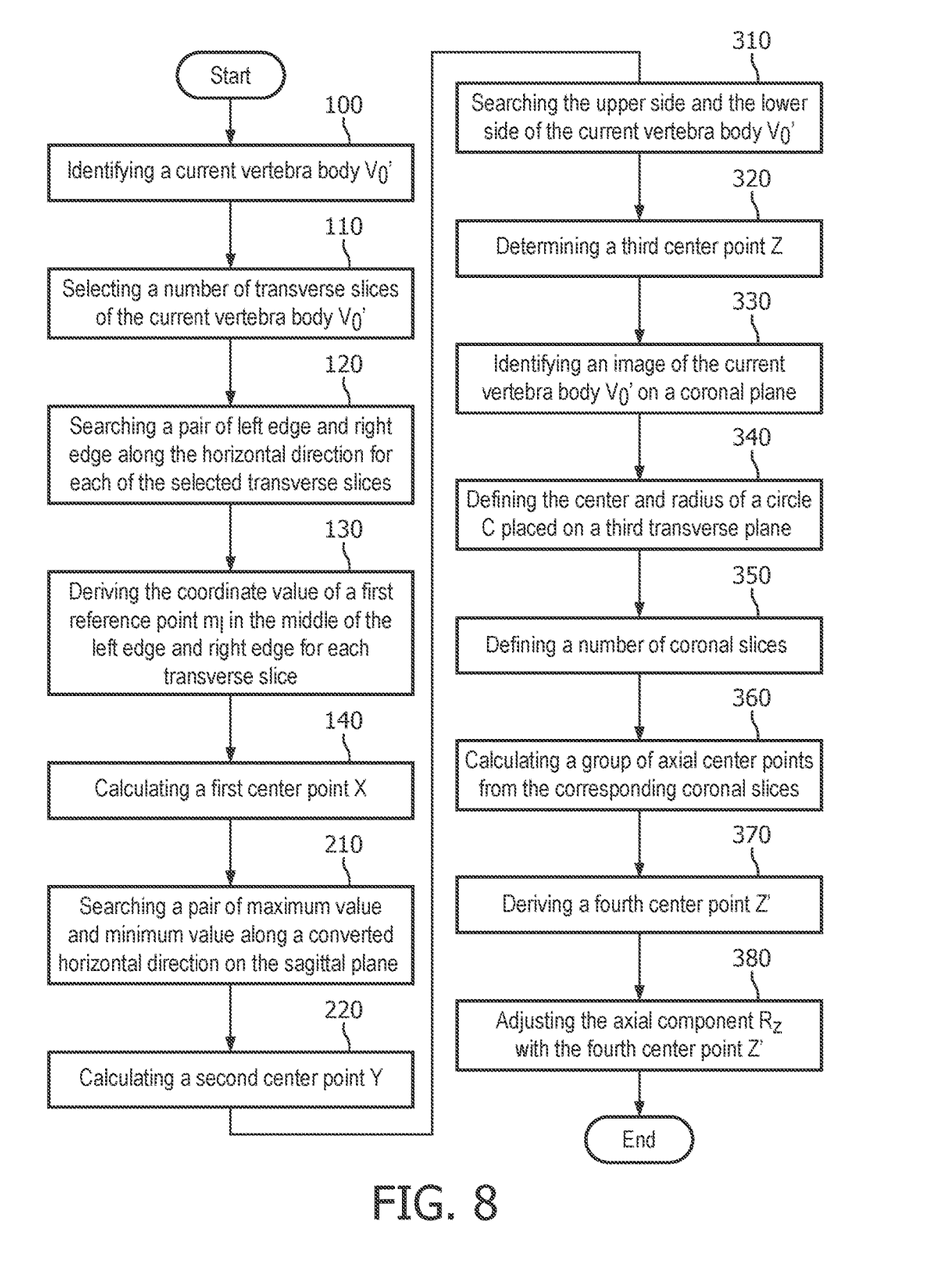
FIG. 8 is a block/flow diagram showing a detection method according to another embodiment of the present disclosure.

FIG. 8 illustrates a block/flow diagram for a detection method in accordance with one embodiment of the present disclosure wherein the 3D components of the initial point is determined automatically.

Figure 9A:
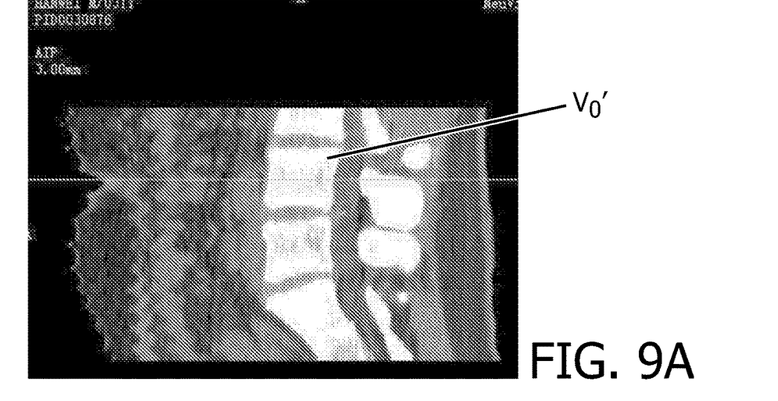
FIG. 9A is a sagittal view of current vertebra body according to another embodiment of the present disclosure.

In block 100, any one of vertebra bodies visible in an image on a sagittal plane is selected as an initial vertebra body. As shown in FIG. 9A, current vertebra body $V_0'$ is identified as the initial vertebra body. 3D components of an initial point R positioned in the center of the current vertebra body $V_0'$ can be obtained by the following steps.

Figure 9B:
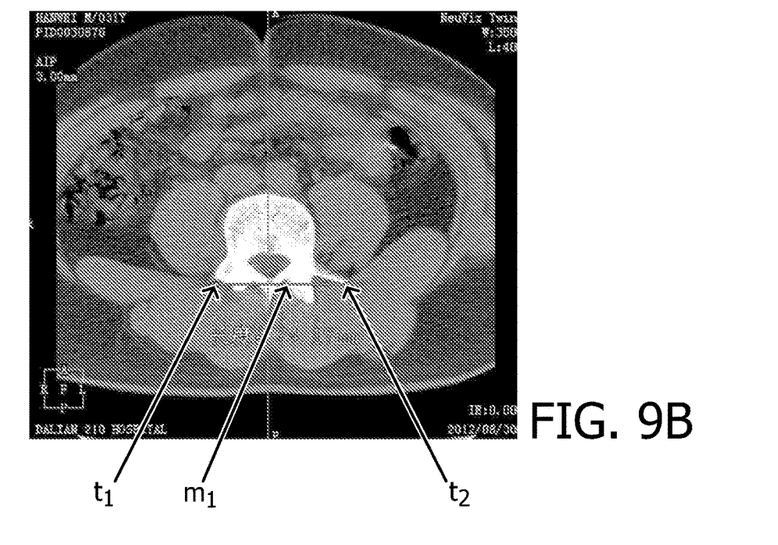
FIG. 9B is a transverse view of the current vertebra body.

In block 110, a number of transverse slices of the current vertebra body $V_0'$ are selected. In block 120, a pair of left edge and right edge $(t_1, t_2)$ of an image along the horizontal direction for each of the selected transverse slices can be searched by the image regional growth as shown in FIG. 9B. In block 130, a first reference point $m_1$ is positioned in the middle of the left edge and right edge $(t_1, t_2)$ of the image along the horizontal direction. The coordinate value of the first reference point $m_1$ can be derived from an average of the coordinate values of the left edge $t_1$ and right edge $t_2$. In block 140, based on the first reference point $m_1$ of each transverse slice, a first center point X as the horizontal component $R_x$ of the initial point R can be calculated as an average of the coordinate value of the first reference point $m_1$ of each transverse slice.

In block 210, a sagittal plane is defined by the horizontal component $R_x$. A pair of maximum value and minimum value $(y_{max}, y_{min})$ for an image of the current vertebra body $V_0'$ along a converted horizontal direction on the sagittal plane can be searched by the image regional growth. In block 220, based on the pair of maximum value and minimum value, a second center point Y as vertical component $R_y$ of the initial point R can be calculated as an average of the maximum value $y_{max}$ and minimum value $y_{min}$.

In block 310, an image of the intervertebral disc on a first transverse plane is quite different from an image of the vertebra body on a second transverse plane. For example, the size of the image of the intervertebral disc identified on the first transverse plane is larger than the image of the vertebra body identified on the second transverse plane. Thus, the upper side and the lower side of the current vertebra body $V_0'$ can be searched by identifying the two intervertebral discs adjacent to the current vertebra body. In block 320, a third center point Z along a converted vertical direction on the sagittal plane as axial component $R_z$ of the initial point R can be determined based on the positions of the two intervertebral discs. In one embodiment, the axial component $R_z$ is an average of axial values of the upper side and the lower side of the current vertebra body $V_0'$.

In another embodiment, the axial component $R_z$ can be further adjusted by the following step:

In block 330, an image of the current vertebra body $V_0'$ is identified on a coronal plane by the image regional growth wherein the coronal plane is defined by the second center point Y.

Figure 9C:
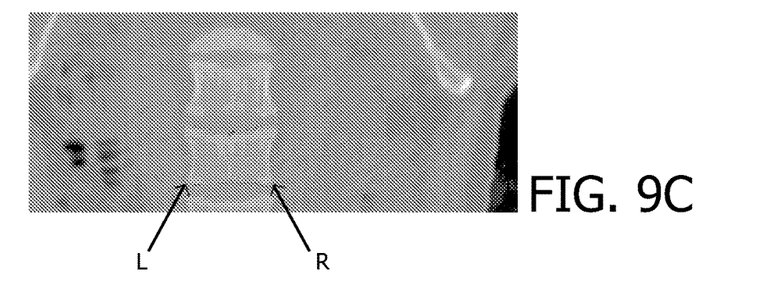
FIG. 9C is a coronal view of the current vertebra body.

In block 340, a second reference point n is defined by the first center point X and the third center point Z on the coronal plane. The left edge L and right edge R of the image on the coronal plane can be searched from the second reference point n and along a horizontal direction of the coronal plane (as shown in FIG. 9C). The half distance between the left edge L and right edge R can be used as the radius of a circle C wherein the circle C is placed on a third transverse plane defined by the third center point Z. On the third transverse plane, the center of the circle C is defined by the first center point X and the second center point Y.

In another embodiment, the first center point X can be updated with the midpoint X' located on a line along the horizontal direction between the left edge L and right edge R of the image on the coronal plane. Thus, the center of the circle C' is defined by the first center point X' and the second center point Y.

Figure 9D:
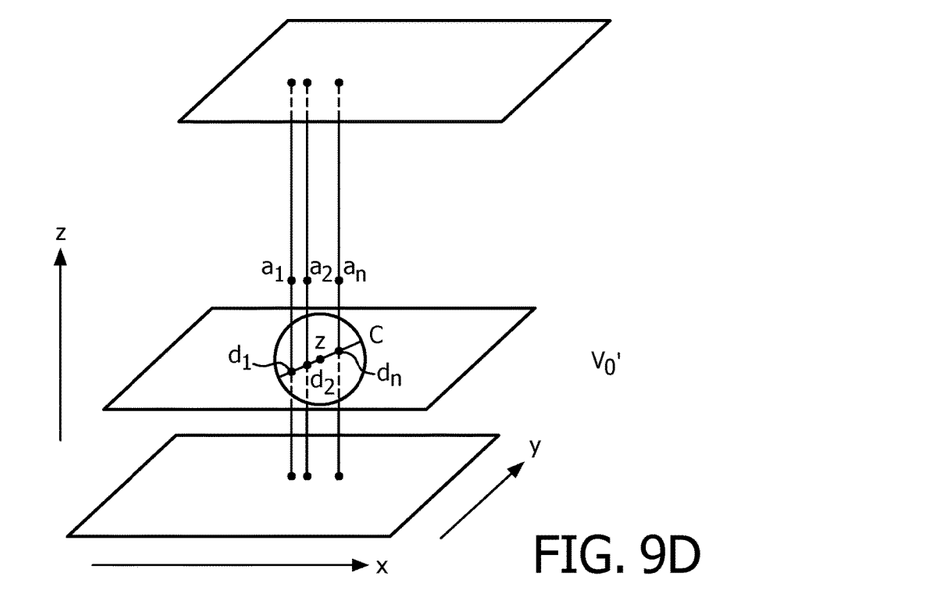
FIG. 9D is an illustration of the mark points according to one embodiment of the present disclosure.

In block 350, a group of mark points $(d_1, d_2 \ldots d_n)$ are selected wherein the mark points $(d_1, d_2 \ldots d_n)$ are positioned on a diameter D1 of the circle C as shown in FIG. 9D. Each mark point (e.g. $d_1$) is served to define a coronal slice (e.g. $s_1$). Thus, a number of coronal slices $(s_1, s_2, \ldots s_n)$ are defined by a group of mark points $(d_1, d_2 \ldots d_n)$ correspondingly.

In block 360, on the coronal slice $s_1$, an axial center point $a_1$ is calculated based on a pair of upper side and lower side of the current vertebra body $V_0'$. In one embodiment, the axial center point $a_1$ is calculated as an average of the coordinate values of the upper side and lower side of the current vertebra body $V_0'$. Similarly, a group of axial center points $(a_1, a_2 \ldots a_n)$ can be obtained from the corresponding coronal slices $(s_1, s_2, \ldots s_n)$.

In block 370, a fourth center point can be derived from the group of axial center points $(a_1, a_2 \ldots a_n)$. In one embodiment, the fourth center point Z' is calculated based on an average of the coordinate values of the group of axial center points $(a_1, a_2 \ldots a_n)$.

In block 380, the axial component $R_z$ of the initial point R is adjusted with the fourth center point Z'.

Figure 9E:
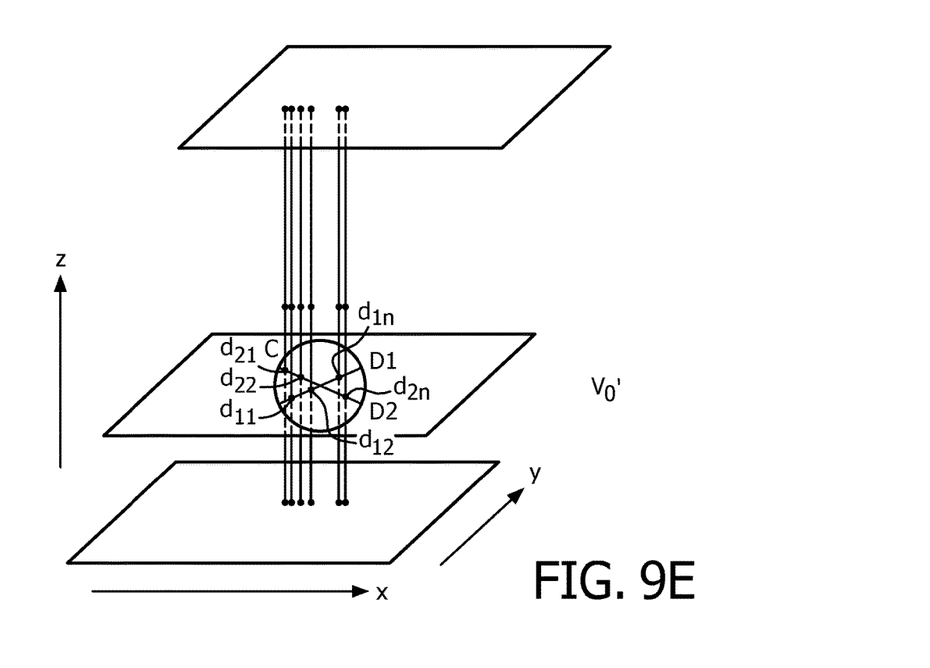
FIG. 9E is an illustration of the mark points according to another embodiment of the present disclosure.

In another embodiment of block 350, a number of groups of mark points are selected wherein each group of the mark points are positioned on a diameter of the circle C. As shown in FIG. 9E, a group of the mark points $(d_{11}, d_{12} \ldots d_{1n})$ are placed on the diameter D1 of the circle C, another group of the mark points $(d_{21}, d_{22} \ldots d_{2n})$ are placed on the diameter D2 of the circle C. Thus, 2n coronal slices can be defined by the two groups of mark points correspondingly. Then, the fourth center point Z" is calculated based on an average of the coordinate values of the two group of axial center points, and the axial component $R_z$ of the initial point R is adjusted with the fourth center point Z". The number of groups of mark points can be selected based on the accuracy of the axial component $R_z$.

Figure 10:
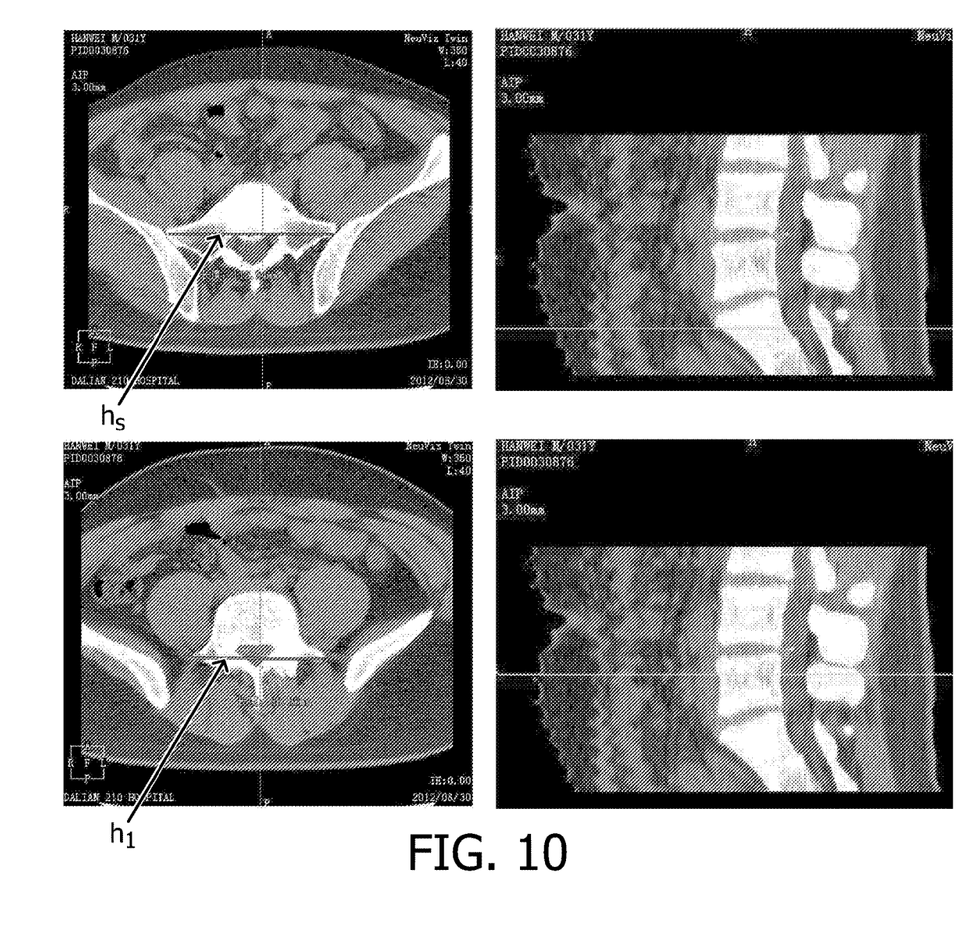
FIG. 10 is an illustration of the last vertebra body and the sacrum.

Once obtaining the 3D components $(R_x, R_y, R_z)$ of the initial point R, the 2D geometrical configuration of the current vertebra body $V_0'$ is obtained by identifying the geometrical parameters of the rectangular template. By performing similar steps described in blocks 20-70, the 2D geometrical configuration of each vertebra body in the upward direction of the current vertebra body $V_0'$ can be detected in sequence. This sequential procedure (i.e. steps in blocks 20-70) can also be carried out on all vertebra bodies in the downward direction of the current vertebra body $V_0'$ to obtain the 2D geometrical configuration of each vertebra body. The last vertebral body can be identified since the horizontal component $h_s$ of an image of sacrum on a transverse plane is quite different from the horizontal component $h_l$ of an image of the last vertebra body on a transverse plane as shown in FIG. 10. In one embodiment, when the 2D geometrical configuration of each vertebra body in the downward direction is detected, the step for identifying the sacrum is performed first. If a detected subject is a vertebra body rather than the sacrum, the sequential procedure (i.e. steps in blocks 20-70) is carried out to obtain the 2D geometrical configuration of the vertebra body.

With the 2D geometrical configuration of each vertebra body, the positions, heights and orientations of intervertebral discs can be determined according to one example of the method as described in conjunction with FIG. 7. Then the transverse images of the intervertebral discs can be formed to serve for diagnosis. Compared with the operator dependent manual measurement, the approach according to the present invention presents a good performance on the accuracy and the speed of the imaging due to a reduction of manual operation in the examination.

It should be understood that the elements described in above blocks may be implemented in various forms of hardware, software or combinations thereof.

Figure 11:
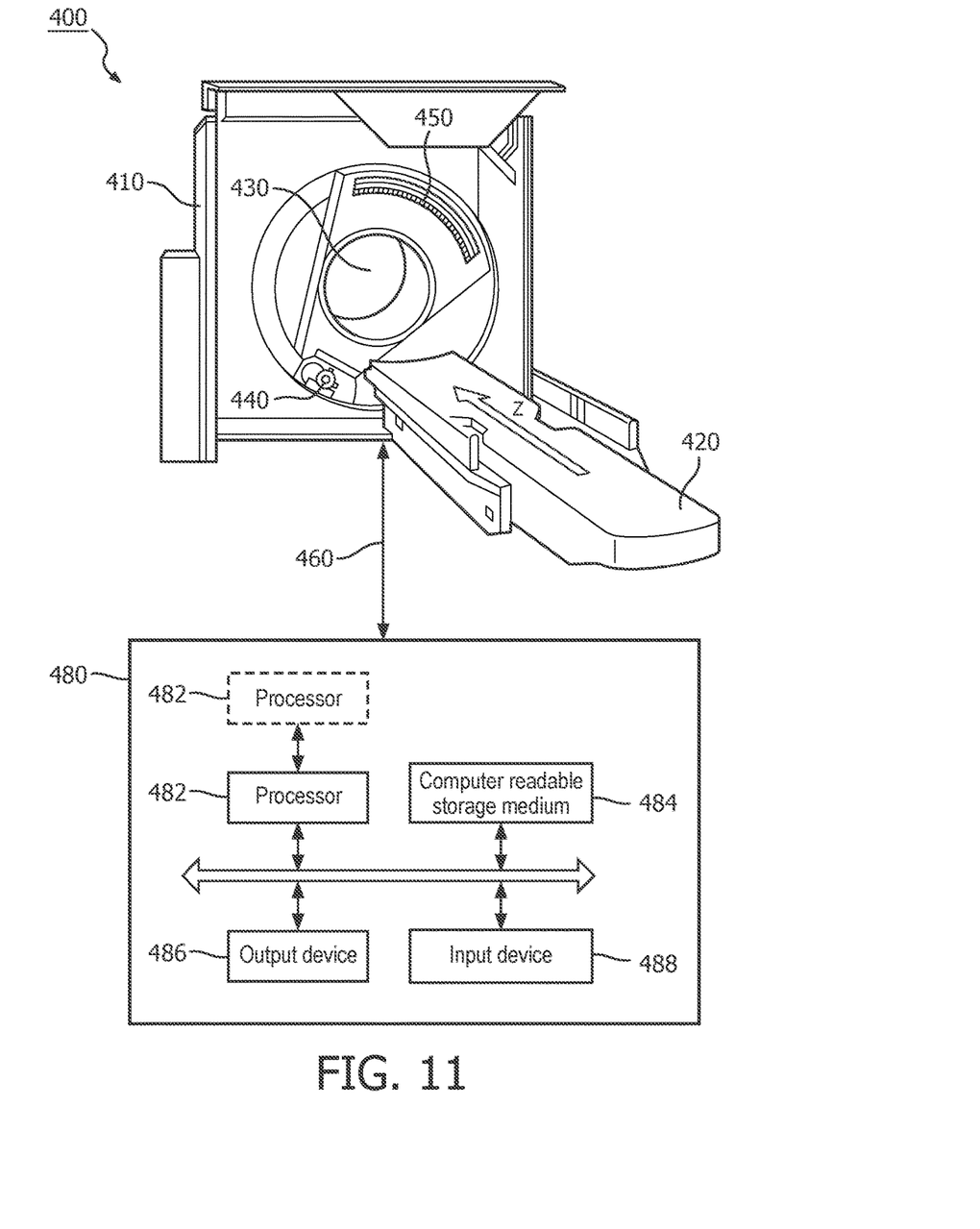
FIG. 11 is an illustration of a CT imaging system according to one embodiment of the present disclosure.

An exemplary CT imaging system 400 is shown in FIG. 11. According to one embodiment, a general-purpose computing system serves as an operator controller 480. The controller 480 includes one or more processors 482 that execute one or more computer readable instructions (i.e. the elements in above blocks implemented in the form of the software) stored or encoded in computer readable storage medium 484 local or remote to the computing system. Software resident on the controller allows the operator to control operation of the system initiating scanning, etc. The controller also includes an output device 486 such as display and an input device 488 such as a keyboard, mouse, touch screen, etc.

As shown in FIG. 11, this CT imaging system 400 includes a gantry 410 and a support 420. A patient or other subject to be imaged (not shown in FIG. 11) lies down on the support 420 and is moved to be disposed within an aperture 430 in the gantry 410. A CT imaging acquisition system comprises an x-ray source 440 and an x-ray detector 450. Once the patient is in position, the x-ray source 440 and the x-ray detector 450 rotate together around the aperture 430 to record CT imaging data. The CT imaging data is supplied to the operator controller 480 through a communication link 460 for the spine position detection.

It should be noted that the above-mentioned solutions illustrate rather than limit the invention and that those skilled in the art would be able to design alternative solutions without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. A method for spine position detection, comprising:
    obtaining 2D geometrical configuration of a current vertebra body selected from a plurality of vertebra bodies visible in an image on a sagittal plane defined by a horizontal component of an initial point, a geometrical template being applied to the current vertebra body and the 2D geometrical configuration of the current vertebra body being adjusted by a predetermined correlation evaluation;
    searching adjacent edge points of next vertebra body corresponding to a number of edge points of the current vertebra body by identifying the gradient values along the direction substantially perpendicular to the edge of the current vertebra body based on the adjusted 2D geometrical configuration of the current vertebra body;
    calculating height of an intervertebral disc located between the current vertebra body and the next vertebra body based on an average of the distances between the edge points of the current vertebra body and the corresponding adjacent edge points of the next vertebra body;
    determining 2D geometrical configuration of the next vertebra body based on the height of the intervertebral disc and the adjusted 2D geometrical configuration of the current vertebra body.

2. The method of claim 1, wherein the geometrical template is a rectangular template with 2D parameter values on the sagittal plane.

3. The method of claim 2, wherein the 2D geometrical configuration comprises center, width, height and orientation of the vertebra body.

4. The method of claim 1, further comprising:
    deriving 2D geometrical information of the intervertebral disc from the adjusted 2D geometrical configuration of the current vertebra body and the adjusted 2D geometrical configuration of the next vertebra body.

5. The method of claim 1, wherein the 2D geometrical information of the intervertebral disc at least comprises center, height and orientation of the intervertebral disc.

6. The method of claim 1, wherein last vertebral body is selected as the current vertebra body and the 2D geometrical configuration of the last vertebra body is obtained by specifying 3D components of the initial point indicated on the center of the last vertebral body.

7. The method of claim 1, further comprising:
    selecting a number of transverse slices of the current vertebra body;
    searching a pair of left edge and right edge of an image along the horizontal direction for each of the transverse slices;
    deriving a first reference point of each transverse slice along the horizontal direction from each pair of the left edge and the right edge of the image;
    calculating, based on the first reference point of each transverse slice, a first center point as the horizontal component of the initial point.

8. The method of claim 7, further comprising:
    searching a pair of maximum value and minimum value for an image of the current vertebra body along a converted horizontal direction on the sagittal plane;
    calculating, based on the pair of maximum value and minimum value, a second center point as vertical component of the initial point.

9. The method of claim 8, further comprising:

identifying two intervertebral discs adjacent to the upper side and the lower side of the current vertebra body based on the size of image of the intervertebral disc on a first transverse plane and the size of image of the vertebra body on a second transverse plane;

determining, based on the positions of the two intervertebral discs, a third center point along a converted vertical direction on the sagittal plane as axial component of the initial point.

10. The method of claim 9, further comprising:

identifying an image of the current vertebra body on a coronal plane defined by the second center point;

searching left edge and right edge of the image on the coronal plane from a second reference point defined by the first center point and the third center point and along a horizontal direction of the coronal plane to determine radius of a circle placed on a third transverse plane defined by the third center point wherein the center of the circle is defined by the first center point and the second center point;

selecting one or more groups of mark points wherein each group of mark points is positioned on a diameter of the circle and each mark point is provided to define a coronal slice;

deriving a fourth center point from a set of axial center points wherein each axial center point is calculated based on a pair of upper side and lower side of the current vertebra body on the coronal slice defined by the mark point;

adjusting the axial component of the initial point with the fourth center point.

11. The method of claim 10, wherein the first center point can be updated with midpoint located on the line between the left edge and right edge of the image on the coronal plane along the horizontal direction.

12. The method of claim 1, further comprising:

identifying last vertebral body based on the horizontal component of an image of sacrum on a fourth transverse plane and the horizontal component of an image of the last vertebra body on a fifth transverse plane.

13. The method of claim 1, wherein the predetermined correlation evaluation comprising a particle filtering.

14. The method of claim 13, wherein range of 2D parameter values for a rectangular template comprises:

$$x \in (Q_0 \cdot x - 10 \text{ mm}, Q_0 \cdot x + 10 \text{ mm})$$
$$y \in (Q_0 \cdot y - 5 \text{ mm}, Q_0 \cdot y + 5 \text{ mm})$$
$$\frac{w}{h} \in (1, 1.5)$$

wherein x is the parameter value along horizontal direction on the sagittal plane, $Q_0 \cdot x$ is the horizontal component of the initial point, y is the parameter values along vertical direction on the sagittal plane, $Q_0 \cdot y$ is the vertical component of the initial point, (w/h) is width-height ratio of the rectangular template.

15. A system for spine position detection, comprising:

a program storage device readable by machine, tangibly embodying a program of instructions executable by the machine to perform the method of claim 1.

16. An x-ray system comprising a CT imaging acquisition system including an x-ray source and an x-ray detector for recording CT imaging data;

a system, being supplied with the CT imaging data, for spine position detection according to claim 15.

* * * * *